(12) United States Patent
Funatsu et al.

(10) Patent No.: US 10,369,295 B2
(45) Date of Patent: Aug. 6, 2019

(54) SYRINGE ASSEMBLY, CAP, AND PUNCTURE NEEDLE

(71) Applicant: TERUMO KABUSHIKI KAISHA, Tokyo (JP)

(72) Inventors: Kaori Funatsu, Kanagawa (JP); Yoshihiko Abe, Kanagawa (JP); Ruriko Iibuchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/470,835

(22) Filed: Mar. 27, 2017

(65) Prior Publication Data

US 2017/0197040 A1    Jul. 13, 2017

Related U.S. Application Data

(63) Continuation of application No. PCT/JP2015/069602, filed on Jul. 8, 2015.

(30) Foreign Application Priority Data

Oct. 1, 2014  (JP) .................................. 2014-203388

(51) Int. Cl.
*A61M 5/28* (2006.01)
*A61M 5/31* (2006.01)
(Continued)

(52) U.S. Cl.
CPC ............ *A61M 5/3202* (2013.01); *A61M 5/28* (2013.01); *A61M 5/285* (2013.01); *A61M 5/32* (2013.01);
(Continued)

(58) Field of Classification Search
CPC ...... A61M 5/3202; A61M 5/28; A61M 5/285; A61M 5/32
(Continued)

(56) References Cited

U.S. PATENT DOCUMENTS 4,964,866 A    10/1990  Szwarc
5,980,495 A    11/1999  Heinz et al.
(Continued)

FOREIGN PATENT DOCUMENTS

JP    3-173576 A      7/1991
JP    10-305098 A    11/1998
(Continued)

OTHER PUBLICATIONS

International Search Report issued in International Patent Application No. PCT/JP2015/069602 dated Aug. 4, 2015.

*Primary Examiner* — Phillip A Gray
(74) *Attorney, Agent, or Firm* — Foley & Lardner LLP (57) ABSTRACT

A syringe assembly includes a barrel having a barrel tip portion, a puncture needle projecting from the barrel tip portion, and a cap that is detachably mountable to the barrel so as to seal a distal end of a needle hole. The cap has a receiving hole that receives the puncture needle, a bottom wall portion into which the puncture needle is inserted, and a stopper portion that defines an insertion length of the puncture needle relative to the bottom wall portion. In a state in which the cap is mounted to the barrel, the length from the most proximal position of a contact region between the cap and the puncture needle to the most proximal position of an edge surface is 1 to 3 mm.

2 Claims, 5 Drawing Sheets

(51) Int. Cl.
    *A61M 5/32*       (2006.01)
    *A61M 5/34*       (2006.01)

(52) U.S. Cl.
    CPC ....... *A61M 5/343* (2013.01); *A61M 2005/311* (2013.01); *A61M 2005/3107* (2013.01)

(58) Field of Classification Search
    USPC ........................................................ 604/265
    See application file for complete search history.

(56) References Cited

U.S. PATENT DOCUMENTS

| | | |
|---|---|---|
| 2001/0039402 A1 | 11/2001 | Prais et al. |
| 2002/0062108 A1 | 5/2002 | Courteix |
| 2012/0330243 A1* | 12/2012 | Liversidge .......... A61M 5/3213 604/198 |

FOREIGN PATENT DOCUMENTS

| | | |
|---|---|---|
| JP | 2004-532060 A | 10/2004 |
| JP | 2013-519415 A | 5/2013 |

\* cited by examiner

SYRINGE ASSEMBLY, CAP, AND PUNCTURE NEEDLE

CROSS-REFERENCE TO RELATED APPLICATIONS

The present application is a bypass continuation of PCT/JP2015/069602, filed on Jul. 8, 2015, which claims priority to Japanese Application No. 2014-203388, filed on Oct. 1, 2014. These applications are hereby incorporated by reference in their entireties.

BACKGROUND

The present disclosure relates to a syringe assembly, a cap, and a puncture needle.

For example, in a prefilled syringe that is filled with a drug liquid or the like in advance, a cap is detachably mounted to a tip portion of a barrel provided with a puncture needle, so as to protect the puncture needle and to seal a needle hole of the puncture needle, to prevent leakage of the drug liquid or the like. Further, it is known in the art to coat an outer surface of a puncture needle with a lubricant such as a silicone oil for the purpose of, for example, lowering the piercing resistance in injecting the drug liquid or the like into a human being or the like and alleviating pain upon piercing (e.g., refer to JP 2013-519415 A).

When the above-described cap is mounted to the tip portion of the barrel, the puncture needle is inserted into the cap so as to seal the needle hole. In this case, a whole or a part of the lubricant applied to the outer surface of the puncture needle may be wiped off, and eventually, the piercing resistance to the patient upon use may increase, and the patient will suffer from increased pain.

SUMMARY

One objective of the present disclosure, which has been made in view of the above problems, is to provide a syringe assembly, a cap, and a puncture needle by which a sufficiently small piercing resistance and a full sealing property are compatible with each other.

A syringe assembly according to one embodiment of the invention comprises: a barrel including a cylindrical barrel body that has an opening at a proximal end thereof and a barrel tip portion disposed at a distal end of the barrel body; a puncture needle having an edge surface and a needle hole and being held by the barrel tip portion so as to project from the barrel tip portion, the puncture needle having a lubricant-covered region on at least a part of an outer surface thereof; and a cap being detachably mountable to the barrel and sealing a distal end of the needle hole, wherein the cap has a receiving hole that receives the puncture needle, a bottom wall portion that is disposed adjacent to a distal end side of the receiving hole and into which the puncture needle is inserted, and a stopper portion that defines an insertion length of the puncture needle relative to the bottom wall portion by abutting against the barrel, and in a state in which the cap is mounted to the barrel, a length from a most proximal position of a contact region between the cap and the puncture needle to a most proximal position of the edge surface is in a range of 1 to 3 mm.

According to the syringe assembly configured in the above-described manner, the length by which the lubricant is wiped off from the outer surface of the puncture needle upon mounting the cap to the distal end portion of the barrel in a production step can be favorably shortened, and also the needle hole of the puncture needle can be fully sealed. Therefore, according to this syringe assembly, a sufficiently small piercing resistance and a full sealing property are compatible with each other.

In the above syringe assembly, a length of the edge surface along an axial direction of the puncture needle may be in a range of 1 to 4 mm. According to this configuration, the length by which the lubricant is wiped off from the outer surface of the puncture needle is restricted, at most, to a range of 3 to 5 mm from the most distal end of the puncture needle, so that a sufficiently small piercing resistance can be more effectively obtained.

In the above syringe assembly, the bottom wall portion preferably has a Shore D hardness in a range of 35 to 55. According to this configuration, a full sealing property can be more effectively obtained.

According to another embodiment of the invention, a cap is configured to be detachably mountable to a barrel of a syringe assembly and to seal a distal end of a needle hole, the syringe assembly comprising: the barrel that includes a cylindrical barrel body having an opening at a proximal end thereof and a barrel tip portion disposed at a distal end of the barrel body; and a puncture needle that has an edge surface and the needle hole and that is held by the barrel tip portion so as to project from the barrel tip portion, the puncture needle having a lubricant-covered region on at least a part of an outer surface thereof, the cap comprising: a receiving hole that is configured to receives the puncture needle; a bottom wall portion that is disposed adjacent to a distal end side of the receiving hole and into which the puncture needle is insertable; and a stopper portion that is configured to define an insertion length of the puncture needle relative to the bottom wall portion by abutting against the barrel, wherein in a state in which the cap is mounted to the barrel, a length from a most proximal position of a contact region between the cap and the puncture needle to a most proximal position of the edge surface is in a range of 1 to 3 mm.

In the above cap, the bottom wall portion preferably has a Shore D hardness in a range of 35 to 55.

According to another embodiment of the invention, a puncture needle has an edge surface and a needle hole, the puncture needle comprising: a first lubricant-covered region formed on an outer surface of the puncture needle; a second lubricant-covered region formed adjacent to an outer surface of a proximal end side of the first lubricant-covered region; and a non-lubricant-covered region formed adjacent to an outer surface of a proximal end side proximal to the second lubricant-covered region, wherein the first lubricant-covered region has a smaller lubricant-covering thickness than the second lubricant-covered region and is formed from a most distal position of the puncture needle to a position that is in a range of 1 to 3 mm proximal to a most proximal position of the edge surface.

According to the puncture needled configured in the above-described manner, the first lubricant-covered region has a smaller lubricant-covering thickness than the second lubricant-covered region, so that the amount of the lubricant can be reduced as compared with a case in which the lubricant is uniformly applied along the axial direction of the puncture needle. Further, though the first lubricant-covered region has a smaller lubricant-covering thickness than the second lubricant-covered region, the length of the first lubricant-covered region is suitably restricted, so that a sufficiently small piercing resistance can be obtained.

According to the syringe assembly, the cap, and the puncture needle of certain embodiments of the present invention, a sufficiently small piercing resistance and a full sealing property are compatible with each other.

DETAILED DESCRIPTION

Hereafter, a syringe assembly, a cap, and a puncture needle according to the present invention will be described by way of example embodiments, with reference to the attached drawings.

Figure 1:
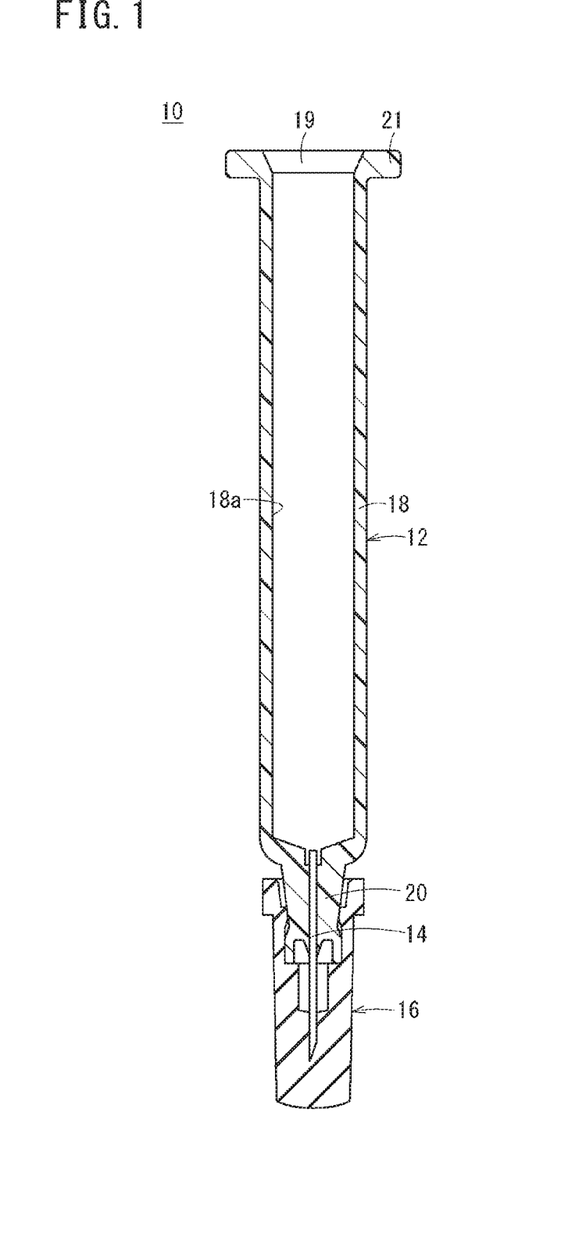
FIG. 1 is a schematic sectional view of a syringe assembly according to one embodiment of the present invention.

FIG. 1 is a schematic sectional view of a syringe assembly 10 according to one embodiment of the present invention. The syringe assembly 10 is provided with a barrel 12 having an interior space 18a formed therein, a puncture needle 14 held by a distal end portion of the barrel 12, and a cap 16 mounted to the distal end portion of the barrel 12.

The syringe assembly 10 according to the present embodiment is configured as a prefilled syringe. That is, the interior of the barrel 12 of the syringe assembly 10 (interior space 18a) is filled with a drug, and further a gasket is inserted at a given position, so as to configure the prefilled syringe. Also, a plunger may be mounted on a proximal end side of the gasket, or the gasket may have a shape such that a plunger can be mounted, in accordance with the needs.

The barrel 12 is a transparent or translucent cylindrical body, which is preferably made of a material having low oxygen permeability and low water vapor permeability. Examples of the material constituting the barrel 12 include resins such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, cyclic polyolefin etc., and glass. Among these, polypropylene or cyclic polyolefin is preferable in view of application to autoclave sterilization.

The barrel 12 is provided with a barrel body 18 having an opening 19 at a proximal end and a barrel tip portion 20 provided at a distal end of the barrel body 18. The interior space 18a is formed in an inside of the barrel body 18. A flange portion 21 is provided at the proximal end of the barrel body 18 so as to surround the opening 19 and to project outward.

Figure 2:
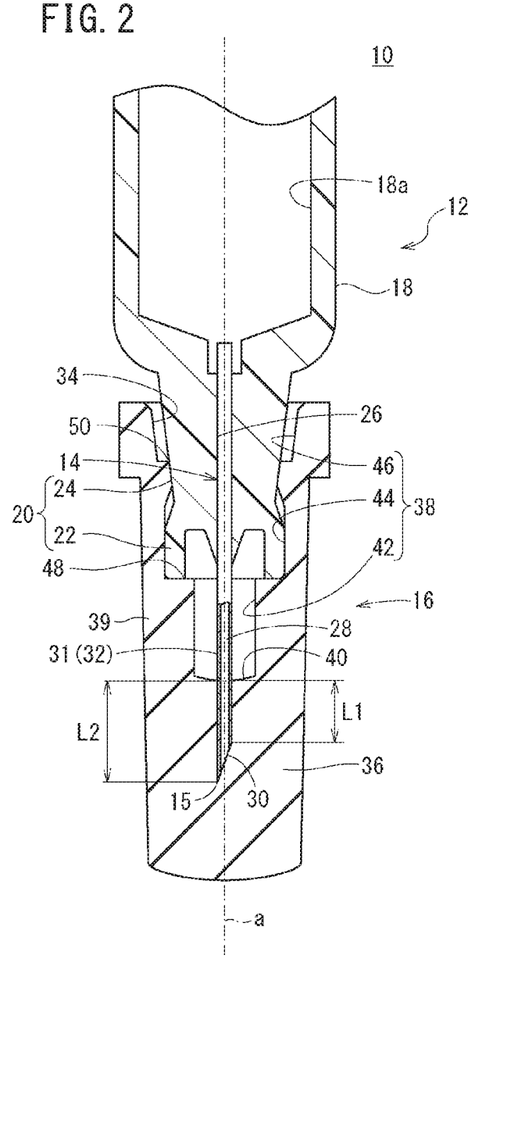
FIG. 2 is an enlarged sectional view of a cap and a site therearound of the syringe assembly shown in FIG. 1.

The barrel tip portion 20 is formed to have a smaller diameter than the barrel body 18 (portions excluding the flange portion 21). Referring to FIG. 2, in the present embodiment, the barrel tip portion 20 has an annular head 22 having a substantially uniform outer diameter along the axial direction and a tapered portion 24 disposed on the proximal end side of this annular head 22, the tapered portion 24 increasing in outer diameter towards the proximal end direction. Further, a hole 26 that penetrates in the axial direction is formed in the barrel tip portion 20. The puncture needle 14 is held by the barrel tip portion 20 to be fixed in position to the barrel tip portion 20 in a state of being inserted into this hole 26. Such fixing can also be formed, for example, by integrally forming the puncture needle 14 and the barrel body 18 through insertion molding.

The puncture needle 14 is a hollow member having a linear shape and is held by the barrel tip portion 20 to project from the barrel tip portion 20 in a distal end direction. A needle hole 28 is formed to penetrate through the puncture needle 14 in its longitudinal direction. This needle hole 28 is in communication with the interior space 18a of the barrel 12. Further, an edge surface 30 that is inclined relative to the axial line of the puncture needle 14 is formed at the distal end portion of the puncture needle 14. The distal end (the most distal end portion) of the edge surface 30 is a needle tip 15 of the puncture needle 14.

The puncture needle 14 is preferably formed of a material having a rigidity that is suitable for puncturing a skin of a patient. Examples of the material constituting the puncture needle 14 such as this include metals such as stainless steel, aluminum alloy, and titanium alloy, and hard resins such as polyphenylene sulfide.

In order to reduce the piercing resistance upon puncturing the skin of the patient with the puncture needle 14, at least a part of an outer surface of the puncture needle 14 has a lubricant-covered region 32 that is covered with a lubricant 31. Specifically, the lubricant-covered region 32 exists from the most distal end portion (needle tip 15) of the puncture needle 14 to a neighborhood of a distal end surface of the barrel tip portion 20. The lubricant 31 that is applied to the lubricant-covered region 32 may be, for example, a liquid lubricant such as a silicone oil.

Figure 3:
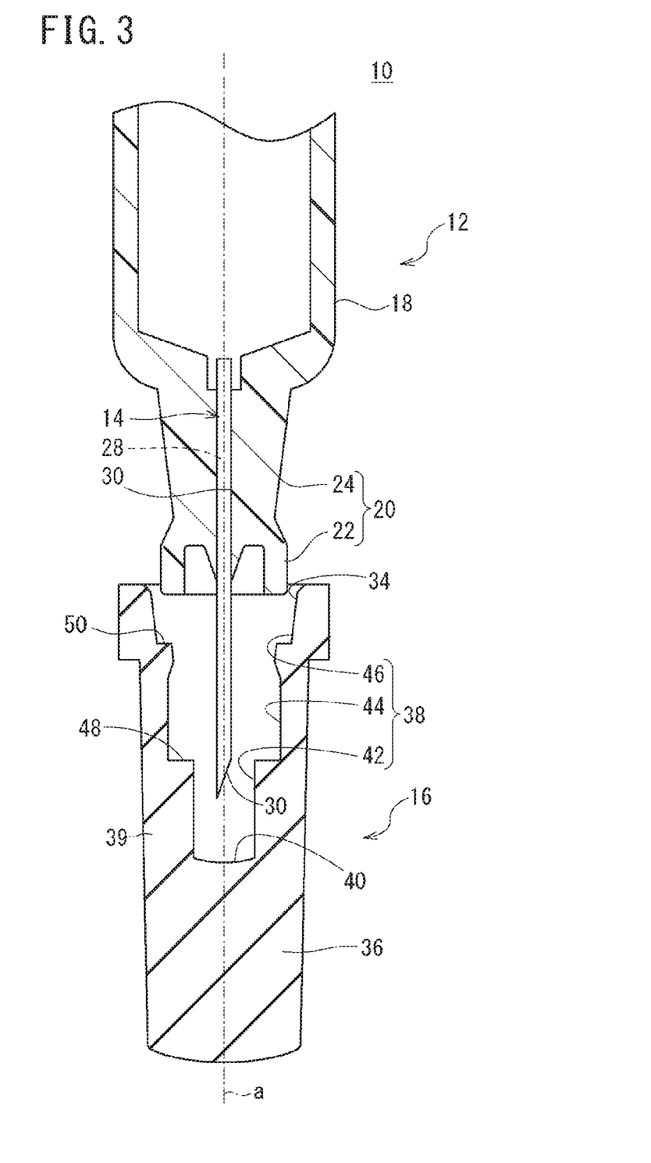
FIG. 3 is an enlarged sectional view illustrating a state before the cap is mounted to a tip portion of a barrel in the syringe assembly shown in FIG. 1.

Referring to FIGS. 2 and 3, the cap 16 has a bottomed cylindrical shape having an open end portion 34 at one end and a thick bottom wall portion 36 at the other end. Referring to FIG. 2, the puncture needle 14 is inserted into the bottom wall portion 36 in a state in which the cap 16 is mounted to the barrel 12. In the present embodiment, the whole of the cap 16 is formed of an elastic member.

Examples of the material constituting the cap 16 include rubbers such as isoprene rubber, butyl rubber, latex rubber, and silicone rubber, and elastomers such as SBS elastomer, SEBS elastomer, and polyolefin elastomer. In order to obtain a desired sealing property of the cap 16 on the needle hole 28 of the puncture needle 14, the material constituting the cap 16 (particularly the bottom wall portion 36) preferably has a Shore D hardness of, for example, 35 to 55. Further, the compression set (JIS K 3262) of the material constituting the cap 16 (particularly the bottom wall portion 36) is preferably in a range of 10% to 24%, for example, from the viewpoint of improving the sealing property and preventing leakage of liquid from the needle tip 15.

A receiving hole 38 extending along the axis of the cap 16 is formed in the inside of the bottom wall portion 36 of the cap 16 and a side wall 39 extending from the bottom wall portion 36 toward the open end portion 34. The puncture needle 14 and the barrel tip portion 20 can be inserted into this receiving hole 38 from the open end portion 34 toward the bottom wall portion 36.

In the present embodiment, the receiving hole 38 includes a small diameter portion 42, an intermediate diameter portion 44, and a large diameter portion 46 in that order from a proximal end surface 40 of the bottom wall portion 36 toward the open end portion 34, each portion having a different inner diameter.

Specifically, the receiving hole 38 includes the intermediate diameter portion 44 having an inner diameter smaller than an outer diameter of the annular head 22; a stopper portion 48 provided at the distal end of the intermediate diameter portion 44; the small diameter portion 42 that is formed from the stopper portion 48 toward the bottom wall portion 36 and has an inner diameter smaller than the inner diameter of the intermediate diameter portion 44; and the large diameter portion 46 having an inner diameter larger than the outer diameter of the annular head 22.

The small diameter portion 42 is a portion where the inner diameter of the receiving hole 38 attains the minimum, and the inner diameter of the small diameter portion 42 is larger than the outer diameter of the puncture needle 14. Therefore, the inner circumferential surface of the receiving hole 38 (specifically, the inner circumferential surface of the small diameter portion 42) is not in contact with the outer surface of the puncture needle 14 and is not in contact with the lubricant 31 that covers the outer surface of the puncture needle 14.

In the present embodiment, the stopper portion 48 is a step difference based on a difference in inner diameter between the small diameter portion 42 and the intermediate diameter portion 44. When the barrel tip portion 20 is inserted into the receiving hole 38, the stopper portion 48 abuts against the distal end surface of the barrel tip portion 20 to define a final insertion position of the barrel tip portion 20 and an insertion length of the puncture needle 14 relative to the bottom wall portion 36. That is, the stopper portion 48 restricts the entry of the barrel tip portion 20 into the receiving hole 38 beyond the final insertion position of the barrel tip portion 20.

In place of the stopper portion 48 formed by the difference in inner diameter between the small diameter portion 42 and the intermediate diameter portion 44, a different stopper portion that abuts against the barrel body 18 to define the final insertion position of the barrel tip portion 20 and the insertion length of the puncture needle 14 relative to the bottom wall portion 36 may be provided at the proximal end portion of the cap 16.

Further, a temporary stopper portion 50 is formed between the intermediate diameter portion 44 and the large diameter portion 46. During the process of inserting the barrel tip portion 20 to the final insertion position in the receiving hole 38 and detachably mounting the cap 16 to the barrel tip portion 20, the temporary stopper portion 50 performs a function of temporarily stopping the entry of the barrel tip portion 20 into the receiving hole 38. Here, the temporary stopper portion 50 may be omitted in some cases.

In the present embodiment, an entirety of the cap 16 is formed of an elastic member. However, in a modification of the cap 16, the cap may have a bottomed hollow cylindrical cap body that is detachably mounted to the barrel 12 and formed of a hard material (for example, a hard resin, a metal, or the like) and a sealing portion (bottom wall) disposed in the inside of the cap body and formed of an elastic member into which the puncture needle 14 can be inserted to seal the needle hole 28 of the puncture needle 14.

In another modification of the cap 16, the receiving hole 38 may be a hole that is tapered to have a smaller diameter towards the distal end direction.

In the present embodiment, the cap 16 is detachably mounted to the barrel tip portion 20; however, in still another modification of the cap 16, the cap 16 may be detachably mounted to a distal end portion of the barrel body 18 instead of being mounted to the barrel tip portion 20.

The syringe assembly 10 is configured in such a manner that, in a state in which the cap 16 is mounted to the barrel 12, a length L1 from the most proximal position of a contact region between the cap 16 and the puncture needle 14 to the most proximal position of the edge surface 30 (hereafter referred to also as "insertion length L1 to the proximal end of the edge surface") is in a range of 1 to 3 mm. Here, the "state in which the cap 16 is mounted to the barrel 12" refers to a state in which the cap 16 is mounted to the barrel 12 so that the barrel tip portion 20 is inserted to a given maximum insertion depth relative to the receiving hole 38, as shown in FIG. 2.

In the present embodiment, the inner circumferential surface of the small diameter portion 42 is not in contact with the outer surface of the puncture needle 14, so that the most proximal position of the contact region between the cap 16 and the puncture needle 14 coincides with the most proximal position of a portion which is a part of the puncture needle 14 and which is inserted into the bottom wall portion 36 (the proximal end surface 40 of the bottom wall portion 36).

Further, the length of the edge surface 30 (edge surface length) along the axial direction of the puncture needle 14 is preferably in a range of 1 to 4 mm, more preferably in a range of 1 to 2 mm. Furthermore, in a state in which the cap 16 is mounted to the barrel 12, a length L2 from the most proximal position of the contact region between the cap 16 and the puncture needle 14 to the most distal position (needle tip 15) of the puncture needle 14 (hereafter referred to also as "insertion length L2 to the distal end of the edge surface") is preferably in a range of 2 to 7 mm, more preferably in a range of 3 to 5 mm, in consideration of an ordinary edge surface length.

Next, in the step of producing the syringe assembly 10 configured in the above-described manner, a process of detachably mounting the cap 16 to the barrel tip portion 20 of the barrel 12 will be described.

Referring to FIG. 3, the cap 16 and the barrel 12 are relatively positioned so that the axis of the puncture needle 14 is aligned with the axis a of the receiving hole 38 and the distal end of the puncture needle 14 faces the open end portion 34. Further, the cap 16 and the barrel 12 are then relatively moved toward each other along the axis a so that the puncture needle 14 and the tip portion 20 of the barrel 12 are inserted into the receiving hole 38.

During this, before the puncture needle 14 and the barrel tip portion 20 are inserted into the intermediate diameter portion 44 and the small diameter portion 42, the puncture needle 14 and the barrel tip portion 20 are inserted into the large diameter portion 46 having a larger diameter than the intermediate diameter portion 44 and the small diameter portion 42, and the distal end surface of the annular head 22 abuts against the temporary stopper portion 50. This allows that the insertion of the puncture needle 14 and the barrel tip portion 20 is temporarily stopped (once stopped), thereby leading to a state in which the axis a of the receiving hole 38 and the axis of the puncture needle 14 are substantially aligned with each other.

Thereafter, when the puncture needle 14 and the barrel tip portion 20 are further inserted, the annular head 22 advances into an inside of the intermediate diameter portion 44 by overriding the temporary stopper portion 50. By this process, the inner circumferential surface of the intermediate diameter portion 44 is brought into close contact with the outer circumferential surface of the annular head 22, so that an airtight seal is formed between the intermediate diameter portion 44 and the barrel tip portion 20, and the distal end of the puncture needle 14 begins to be inserted into the bottom wall portion 36 from the proximal end surface 40.

Referring to FIG. 2, when the annular head 22 advances through the inside of the intermediate diameter portion 44 and reaches the final insertion position, the distal end surface of the annular head 22 abuts against the stopper portion 48. This restricts further advancement of the barrel tip portion 20 into the receiving hole 38, thereby leading to a state in which the cap 16 is mounted at a given position relative to the barrel 12.

In this case, in accordance with the insertion of the puncture needle 14 into the bottom wall portion 36, a part of the lubricant 31 that covers the outer surface of the puncture needle 14 is wiped off by the proximal end surface 40 of the bottom wall portion 36. That is, the lubricant 31 is wiped off and removed from the outer surface of the portion that is a part of the puncture needle 14 and that is inserted into the bottom wall portion 36 (hereafter referred to as "inserted portion of the puncture needle 14"). However, strictly speaking, on the outer surface of the inserted portion of the puncture needle 14, the lubricant 31 is not completely wiped off, so that a slight thickness of the lubricant 31 exists. This is schematically shown in FIG. 4.

Figure 4:
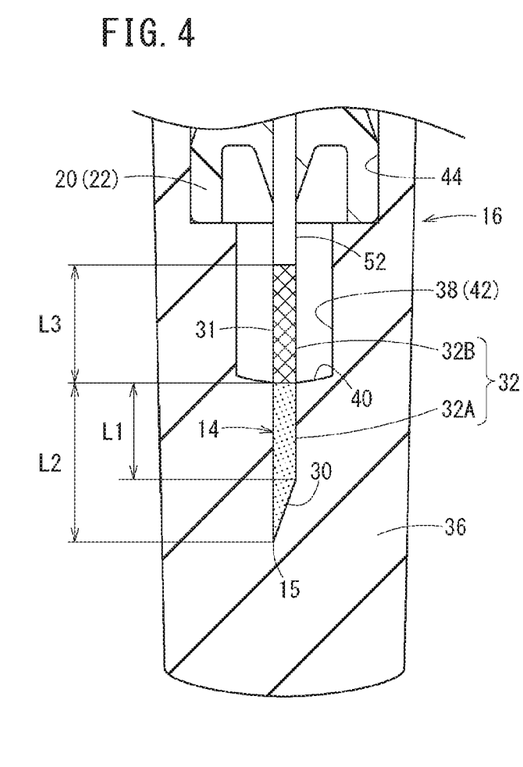
FIG. 4 is a sectional model view for describing a first lubricant-covered region and a second lubricant-covered region in a puncture needle.

Referring to FIG. 4, the puncture needle 14 (portion profecting from the barrel tip portion 20) includes a first lubricant-covered region 32A (region shown by numerous dots), a second lubricant-covered region 32B (region shown by cross-hatching), and a non-lubricant-covered region 52 in that order from the distal end side to the proximal end side. The lubricant-covered region 32 described above is composed of the first lubricant-covered region 32A and the second lubricant-covered region 32B.

The first lubricant-covered region 32A is a site where the covering thickness of the lubricant 31 is smaller than that in the second lubricant-covered region 32B because the lubricant 31 has been wiped off and removed upon insertion of the puncture needle 14 into the bottom wall portion 36. That is, the inserted portion of the puncture needle 14 corresponds to the first lubricant-covered region 32A. Therefore, the first lubricant-covered region 32A is formed from the most distal position (needle tip 15) of the puncture needle 14 to a position that is in a range of 1 to 3 mm proximal to the most proximal position of the edge surface 30. Further, the length of the first lubricant-covered region 32A is equal to the insertion length L2 up to the distal end of the edge surface described above, and is preferably in a range of 2 to 7 mm, more preferably in a range of 3 to 5 mm.

The lubricant-covering thickness of the second lubricant-covered region 32B is preferably, for example, in a range of 0.1 to 5 μm, more preferably in a range of 0.2 to 3 μm. The length L3 of the second lubricant-covered region 32B is preferably larger than the insertion length L1 up to the proximal end of the edge surface, and is preferably, for example, in a range of 3 to 5 mm. The non-lubricant-covered region 52 is a site that is originally not covered with the lubricant 31.

As described above, the syringe assembly 10 is configured in such a manner that, in a state in which the cap 16 is mounted to the barrel 12, the length L1 from the most proximal position of the contact region between the cap 16 and the puncture needle 14 to the most proximal position of the edge surface 30 is in range of 1 to 3 mm. By setting the insertion length L1 of the puncture needle 14 to the proximal end of the edge surface to be 1 mm or more in this manner, the needle hole 28 of the puncture needle 14 can be fully sealed. Further, by setting the insertion length L1 of the puncture needle 14 to the proximal end of the edge surface to be 3 mm or less, the length by which the lubricant 31 is wiped off from the outer surface of the puncture needle 14 upon insertion of the puncture needle 14 into the bottom wall portion 36 can be shortened. As a result, increase in the piercing resistance can be suppressed as much as possible. That is, a sufficiently small piercing resistance can be obtained.

Next, a test that was carried out for confirming the effects of example embodiments of the present invention will be described.

In accordance with a blending preparation shown in the following Tables 1 and 2, unvulcanized rubber blended products A to H were prepared as a material of the cap. With use of a given shaping mold, each of these unvulcanized rubber blended products was pressed and heated so as to perform cross-linking, thereby to form the cap. For each of the obtained samples, the compression set (in accordance with JISK 6262) and the hardness (ShoreDhardness) were evaluated.

TABLE 1

| | Isoprene rubber (parts by weight) | Filler (parts by weight) | Shore D hardness | Compression set (%) |
|---|---|---|---|---|
| A | 100 | 11 | 30 | 6 |
| B | 100 | 18 | 35 | 10 |
| C | 100 | 33 | 45 | 17 |
| D | 100 | 43 | 55 | 24 |
| E | 100 | 67 | 60 | 28 |

TABLE 2

| | Butyl rubber (parts by weight) | Filler (parts by weight) | Shore D hardness | Compression set (%) |
|---|---|---|---|---|
| F | 100 | 11 | 30 | 8 |
| G | 100 | 25 | 45 | 15 |
| H | 100 | 54 | 60 | 24 |

Next, with use of a puncture needle of 27 G (gauge) (having an edge surface length of 2.0 mm), a barrel that is equipped with the needle and to which the above-mentioned cap can be mounted was prepared. Further, after a lubricant (silicone oil; having a viscosity of 12500 cst) was applied to a distal end portion of the puncture needle, the cap A to H described above was mounted, thereby to form a syringe assembly in which a needle tip of the puncture needle had been inserted into the cap. Further, a puncture needle of 29 G was prepared in addition, and a syringe assembly in which the above-mentioned cap C (having a Shore D hardness of 45) had been mounted was prepared for comparison.

In mounting the cap, the insertion length to the proximal end of the edge surface and the insertion length to the distal end of the edge surface were set to be 0.5 to 4.0 mm and 2.5 to 6.0 mm, respectively, as shown in Tables 3 to 5. Further, each of these was sterilized with a high-pressure vapor, thereby to prepare a sterilized syringe assembly.

Piercing Resistance Test

With respect to the sterilized syringe assembly prepared in the above-described manner, the piercing resistance (maximum piercing resistance and barrel resistance) was measured. Specifically, the cap was dismounted and, with use of an autograph (AGS-H manufactured by Shimadzu Corporation), each puncture needle was allowed to pierce into a silicone rubber (having a thickness of 0.5 mm) at a speed of 50 mm/min., so as to measure the maximum resistance value (maximum piercing resistance) up to the time at which the puncture needle pierced by 5 mm from the needle tip and the maximum resistance value (barrel resistance) after the puncture needle passed by 5 mm from the needle tip. Samples in which the maximum piercing resistance was less than 0.2 N and the barrel resistance was less than 0.06 N were determined as "good", and samples in which the maximum piercing resistance was 0.2 N or more or the barrel resistance was 0.06 N or more were determined as "permissible". The results of the piercing resistance test are shown in the following Tables 3 to 5.

Sealing Property Test (Pressure Resistance Test)

On the basis of the "airtight property" test described in JIS T 3210 (revised on 2011/07/29), a test was carried out. Into a barrel from which water had been sufficiently wiped off, water was sucked in up to a position of ¾ of the barrel. After the barrel was sealed with a cap, a pressure of 400 kPa and 200 kPa was applied to a plunger, so as to measure the pressure resistance performance. Samples in which no leakage was recognized were determined as having a pressure resistance (OK), and samples in which leakage was recognized were determined as having no pressure resistance (NG). The results of the sealing property test are shown in the following Tables 3 to 5.

Here, in each frame showing the test results of the samples in Tables 3 to 5, the upper row shows the evaluation (good/permissible) of the piercing resistance test, where the left side shows the maximum piercing resistance (good when the maximum piercing resistance is less than 0.2 N), and the right side shows the barrel resistance (good when the barrel resistance is less than 0.06 N). Further, in each frame, the lower row shows the determination of pass or fail (OK/NG) of the sealing property test, where the left side shows the determination result when a pressure of 200 kPa was applied, and the right side shows the determination result when a pressure of 400 kPa was applied.

TABLE 3

| 27G·isoprene | | A(30) (Shore D hardness) | B(35) | C(45) | D(55) | E(60) |
|---|---|---|---|---|---|---|
| Insertion length to base end of edge surface (Insertion length to tip end of edge surface) | 0.5 mm (2.5 mm) | Good 0.14N, 0.03N NG   NG | Good 0.14N, 0.03N NG   NG | Good 0.14N, 0.04N OK   NG | Good 0.14N, 0.04N OK   NG | Good 0.14N, 0.04N OK   NG |
| | 1 mm (3 mm) | Good 0.14N, 0.03N OK   NG | Good 0.15N, 0.04N OK   OK | Good 0.17N, 0.04N OK   OK | Good 0.18N, 0.04N OK   OK | Permissible 0.20N, 0.05N OK   OK |
| | 2 mm (4 mm) | Good 0.15N, 0.03N OK   NG | Good 0.15N, 0.04N OK   OK | Good 0.17N, 0.04N OK   OK | Good 0.18N, 0.04N OK   OK | Permissible 0.20N, 0.05N OK   OK |
| | 3 mm (5 mm) | Good 0.15N, 0.04N OK   NG | Good 0.16N, 0.04N OK   OK | Good 0.17N, 0.04N OK   OK | Good 0.18N, 0.05N OK   OK | Permissible 0.21N, 0.05N OK   OK |
| | 4 mm (6 mm) | Permissible 0.19N, 0.06N OK   OK | Permissible 0.19N, 0.06N OK   OK | Permissible 0.20N, 0.07N OK   OK | Permissible 0.20N, 0.07N OK   OK | Permissible 0.22N, 0.08N OK   OK |

TABLE 4

| 29G·isoprene | | (Shore D hardness) C(45) |
|---|---|---|
| Insertion length to base end of edge surface (Insertion length to tip end of edge surface) | 0.5 mm (2.5 mm) | OK 0.12N, 0.04N NG |
| | 1 mm (3 mm) | |
| | 2 mm (4 mm) | OK 0.14N, 0.04N OK |
| | 3 mm (5 mm) | |
| | 4 mm (6 mm) | NG 0.20N, 0.06N OK |

TABLE 5

| 27G·butyl | | (Shore D hardness) | | |
|---|---|---|---|---|
| | | F(30) | G(45) | H(60) |
| Insertion length to base end of edge surface (Insertion length to tip end of edge surface) | 0.5 mm (2.5 mm) | | | |
| | 1 mm (3 mm) | | | |
| | 2 mm (4 mm) | OK 0.16N, 0.04N NG | OK 0.17N, 0.04N OK | NG 0.20N, 0.07N OK |
| | 3 mm (5 mm) | | | |
| | 4 mm (6 mm) | | | |

From the above test results, it has been found that, in the samples in which the insertion length to the proximal end of the edge surface is 0.5 mm (the insertion length to the distal end of the edge surface is 2.5 mm), a sufficient sealing property is not obtained, whereas in the samples in which the insertion length to the proximal end of the edge surface is 4 mm (the insertion length to the distal end of the edge surface is 6 mm), the piercing resistance is too large when comparison is made in the same hardness. Further, among the samples in which the insertion length to the proximal end of the edge surface is 1 mm, 2 mm, or 3 mm, the samples (A, F) having a Shore D hardness of 30 can be regarded as having a sealing property that does not raise a problem in practical use, because there is little leakage at 200 kPa though the sealing property at 400 kPa has been tentatively determined as NG. Further, among the samples in which the insertion length to the proximal end of the edge surface is 1 mm, 2 mm, or 3 mm, the samples (E, H) having a Shore D hardness of 60 can be regarded as having a piercing resistance of a degree that does not raise a problem in practical use, though the piercing resistance has been determined to be "permissible". On the other hand, it has been found out that, in the samples in which the insertion length to the proximal end of the edge surface is 1 to 3 mm (the insertion length to the distal end of the edge surface is 3 to 5 mm) and in which the cap has a Shore D hardness of 35 to 55, the piercing resistance is sufficiently small, and a full sealing property is exhibited.

As is clear from the above description, the syringe assembly 10 is configured in such a manner that, in a state in which the cap 16 is mounted to the barrel 12, the length L1 from the most proximal position of the contact region between the cap 16 and the puncture needle 14 to the most proximal position of the edge surface 30 is in a range of 1 to 3 mm, so that the length by which the lubricant 31 is wiped off and removed from the outer surface of the puncture needle 14 upon mounting the cap 16 to the distal end portion of the barrel 12 in a production step can be suitably shortened, and also the needle hole 28 of the puncture needle 14 can be fully sealed. Therefore, according to this syringe assembly 10, a sufficiently small piercing resistance and a full sealing property are compatible with each other.

Furthermore, in the present embodiment, in a state in which the cap 16 is mounted to the barrel 12, the length from the most proximal position of the contact region between the cap 16 and the puncture needle 14 to the most distal position of the puncture needle 14 is in a range of 3 to 5 mm. This configuration allows that the length by which the lubricant 31 is wiped off from the outer surface of the puncture needle 14 is restricted, at most, to a range of 3 to 5 mm from the most distal position of the puncture needle 14, so that a sufficiently small piercing resistance can be obtained with certainty. Further, because the length of the edge surface 30 along the axial direction of the puncture needle 14 is in a range of 1 to 4 mm, a sufficiently small piercing resistance can be obtained with certainty.

Furthermore, in the present embodiment, the bottom wall portion 36 of the cap 16 has a Shore D hardness in range of 35 to 55, so that a full sealing property can be more effectively obtained.

In the present embodiment described above, the syringe assembly 10, the cap 16, and the puncture needle 14 are configured for a prefilled syringe; however, it goes without saying that an object of application of the present invention is not limited to a prefilled syringe, so that the present invention can be applied to other kinds of syringes.

Figure 5:
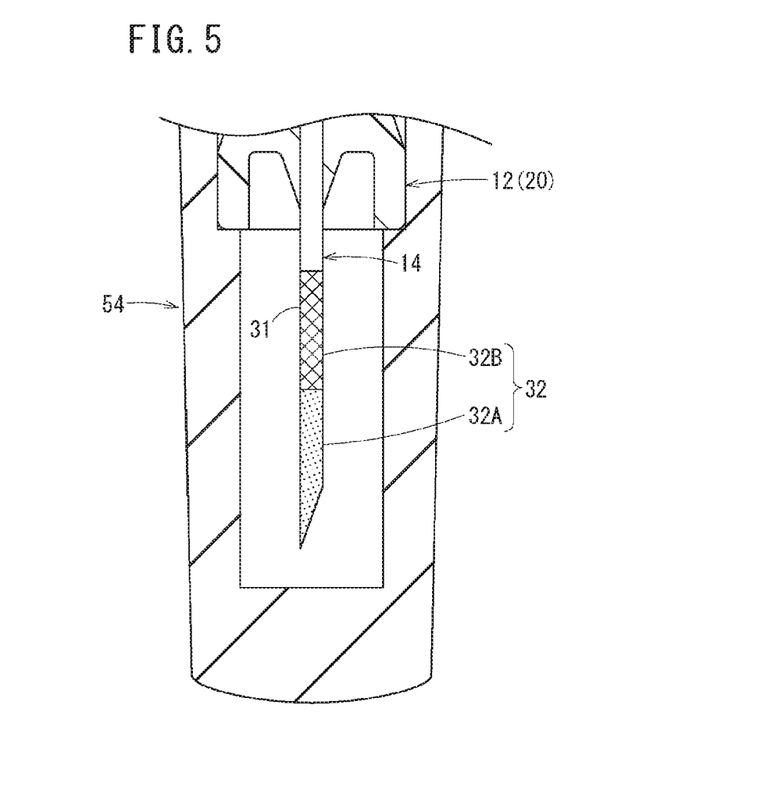
FIG. 5 is sectional model view illustrating another application example of a puncture needle.

As has been described with reference to FIG. 4, in the present embodiment, the puncture needle 14 is provided with the first lubricant-covered region 32A formed on the outer surface, the second lubricant-covered region 32B formed adjacent to the outer surface of the proximal end side of the first lubricant-covered region 32A, and the non-lubricant-covered region 52 formed adjacent to the outer surface of the proximal end side proximal to the second lubricant-covered region 32B, where the first lubricant-covered region 32A has a smaller lubricant-covering thickness than the second lubricant-covered region 32B and is formed from the most distal position of the puncture needle 14 to the position that is in range of 1 to 3 mm proximal to the most proximal position of the edge surface 30. The puncture needle 14 such as this may be applied to a configuration in which a cap 54 that covers the puncture needle 14 in a state of non-contact to the puncture needle 14 is detachably mounted to the barrel 12, as shown in FIG. 5.

According to this configuration, the first lubricant-covered region 32A has a smaller lubricant-covering thickness than the second lubricant-covered region 32B, so that the amount of the lubricant 31 can be reduced as compared with a case in which the lubricant 31 is uniformly applied along the axial direction of the puncture needle 14. Further, though the first lubricant-covered region 32A has a smaller lubricant-covering thickness than the second lubricant-covered region 32B, the length of the first lubricant-covered region 32A is suitably restricted, so that a sufficiently small piercing resistance can be obtained.

While the present invention has been described above with reference to an embodiment, the present invention is not limited thereto. It should be understood that various modifications can be made without departing from the scope of the invention.

The invention claimed is:

1. A syringe assembly comprising:
 a barrel comprising:
  a cylindrical barrel body that includes an opening at a proximal end thereof, and
  a barrel tip portion that is disposed at a distal end of the barrel body;
 a puncture needle that includes an edge surface and a needle hole, and being held by the barrel tip portion so as to project from the barrel tip portion; and
 a cap that is detachably mountable to the barrel so as to seal a distal end of the needle hole;
 wherein the cap includes:
  a receiving hole configured to receive the puncture needle,
  a bottom wall portion that is disposed adjacent to a distal end side of the receiving hole and into which the puncture needle is insertable, wherein the bottom wall portion has a Shore D hardness in range of 35 to 55, and
  a stopper portion that defines an insertion length of the puncture needle relative to the bottom wall portion by abutting against the barrel;
 wherein, in a state in which the cap is mounted to the barrel, a length from a most proximal position of a contact region between the cap and the puncture needle to a most proximal position of the edge surface is in a range of 1 to 3 mm; and
 wherein the puncture needle comprises:
  a first lubricant-covered region at which an outer surface of the puncture needle is covered by a lubricant, the first lubricant-covered region extending from a most distal position of the puncture needle to a position in a range of 1 to 3 mm from the most proximal position of the edge surface,
  a second lubricant-covered region at which the outer surface of the puncture needle is covered by the lubricant, the second lubricant-covered region being adjacent to a proximal end of the first lubricant-covered region, and
  a non-lubricant-covered region at which the outer surface of the puncture needle is not covered by the lubricant, the non-lubricant-covered region being adjacent to a proximal end of the second lubricant-covered region,
  wherein a thickness of the lubricant in the first lubricant-covered region is lower than a thickness of the lubricant in the second lubricant-covered region.

2. The syringe assembly according to claim 1, wherein a length of the edge surface along an axial direction of the puncture needle is in a range of 1 to 4 mm.

* * * * *